United States Patent [19]
Kitani et al.

[11] Patent Number: 5,788,942
[45] Date of Patent: Aug. 4, 1998

[54] DRY ANALYSIS ELEMENT FOR QUANTITATIVE ANALYSIS OF ANALYTE CONTAINED IN WHOLE BLOOD

[75] Inventors: Toru Kitani, Saitama; Takao Akagi, Kurashiki, both of Japan

[73] Assignee: Fuji Photo Film Co., Ltd., Kanagawa, Japan

[21] Appl. No.: 634,523

[22] Filed: Apr. 18, 1996

Related U.S. Application Data

[63] Continuation of Ser. No. 176,883, Jan. 3, 1994, abandoned, which is a continuation of Ser. No. 599,632, Oct. 18, 1990, abandoned.

[30] Foreign Application Priority Data

| Oct. 18, 1989 | [JP] | Japan | 1-269191 |
| Oct. 18, 1989 | [JP] | Japan | 1-269192 |
| Oct. 18, 1989 | [JP] | Japan | 1-269193 |

[51] Int. Cl.$^6$ .................................. G01N 31/22
[52] U.S. Cl. .................... 422/56; 422/57; 436/169; 436/170; 435/805
[58] Field of Search ............... 422/55–57, 99, 422/152, 101; 436/169, 170, 177, 178; 435/505

[56] References Cited

U.S. PATENT DOCUMENTS

| 4,256,693 | 3/1981 | Kondo et al. | 422/56 |
| 4,477,575 | 10/1984 | Vogel et al. | 436/170 |
| 4,753,776 | 6/1988 | Hillman et al. | 422/101 |
| 4,783,315 | 11/1988 | Arai et al. | 422/56 |
| 4,855,108 | 8/1989 | Masuda | 422/56 |
| 4,933,092 | 6/1990 | Aunet et al. | 210/729 |
| 4,990,457 | 2/1991 | Tanaka et al. | 436/170 |
| 5,023,052 | 6/1991 | Nagotomo et al. | 422/56 |
| 5,130,258 | 7/1992 | Makino et al. | 436/169 |

FOREIGN PATENT DOCUMENTS

| 0160916 | 11/1985 | European Pat. Off. |
| 0226465 | 6/1987 | European Pat. Off. |
| 0278496 | 8/1988 | European Pat. Off. |
| 0298473 | 1/1989 | European Pat. Off. |
| 0327918 | 8/1989 | European Pat. Off. |
| 60-230062 | 11/1985 | Japan |
| 62-103542 | 5/1987 | Japan |
| 57148250 | 9/1996 | Japan |

OTHER PUBLICATIONS

2—Japanese Office Actions mailed Mar. 19, 1996.

*Primary Examiner*—Long V. Le
*Attorney, Agent, or Firm*—McAulay Fisher Nissen Goldberg & Kiel, LLP

[57] ABSTRACT

A dry analysis element for the quantitative analysis of an analyte contained in whole blood comprises a layer exhibiting volume filtration function and a detection layer. The layer exhibiting volume filtration function is made of a cloth selected from microfibrous cloths each having an average fiber diameter of from 0.1 to 10 µm or a napped cloth having an average of from 1 to 30 µm. In a first preferred embodiment, the layer exhibiting volume filtration function is composed of a non-woven cloth having a density of from 0.01 to 0.2 g/cm$^3$ and made of fibers each having an average fiber diameter of from 0.2 to 10 µm. In a second preferred embodiment, the layer exhibiting volume filtration function is composed of a napped cloth having a fiber density per cm$^2$ of from $7.0 \times 10^3$ to $8.2 \times 10^6$, each of the napped fibers having an average diameter of from 1 to 30 microns and an average nap length of 0.5 to 5.0 mm. In a third preferred embodiment, the layer exhibiting volume filtration function is composed of a cloth having a porosity of from 45 to 70% and made of micro filaments each having an average filament diameter of from 0.1 to 7 µm.

21 Claims, 1 Drawing Sheet

FIG. 1

DRY ANALYSIS ELEMENT FOR QUANTITATIVE ANALYSIS OF ANALYTE CONTAINED IN WHOLE BLOOD

This is a continuation of application Ser. No. 08/176,883, filed Jan. 3, 1994, now abandoned, which, in turn, is a continuation of application Ser. No. 07/599,632, filed Oct. 18, 1990, now abandoned.

BACKGROUND OF THE INVENTION

1. Field of the Invention

The present invention relates generally to a dry multi-layered analysis element for the quantitative analysis of an analyte contained in whole blood, and particularly to such an analysis element essentially including, as an integrally laminated layer, a micro-fibrous cloth (a woven fabric, knitted fabric, napped fabric and non-woven fabric).

2. Related Art

The wet process and the dry chemical analysis have been used for the quantitative analysis of various components (analytes) in the body fluids, the examination of which are important as the clinical tests. Examples of such analytes in the body fluids are glucose, bilirubin, BUN (urea nitrogen), uric acid, cholesterol and various enzymes including creatine kinase, GOT (glutamyl oxaloacetate transaminase) and GPT (glutamyl pyruvate transaminase). The dry chemical analysis is a analytical method wherein an analysis element containing a dried analysis reagent system is used in the form of a strip, slide or tape, and improved over the wet process wherein a reagent is used as a solution in that the operation sequence is simplified to find the result of analysis rapidly.

In order to further improve the dry analysis method to make it possible to realize a highly precise chemical analysis by using a minute quantity of liquid sample, dry, integral multi-layered analysis elements have been developed. The analysis elements of this type are disclosed, for example, in Japanese Patent Publication No. 21677/1978 (corresponding to U.S. Pat. No. 3,992,158), Unexamined Japanese Patent Publication No. 164356/1980 (corresponding to U.S. Pat. No. 4,292,272) and Unexamined Japanese Patent Publication No. 222769/1985 (corresponding EP 0 162 302A).

The integral multi-layered analysis element (sometimes referred to simply as "multi-layered analysis element" in the following description) comprises, for example, a transparent support, a reagent layer, a light-reflecting layer (light-shielding layer) and a spreading layer. The reagent layer applied on the transparent support (e.g. a polymer sheet) contains a reagent which reacts with an analyte in the liquid sample to develop or change the color in proportion to the quantity or content of the analyte. The spreading layer is provided to spread the liquid sample spotted thereon uniformly so that the analyte contained in the spotted liquid sample is spread evenly. By the action of the spreading layer, the analyte in the liquid sample is present in a substantially constant ratio within a certain area. This action is referred to as the metering function, spreading function or extending function.

When a minute volume (for example about 10 ul) of a liquid sample, such as blood, is spotted on the surface of the dry analysis element, the spotted blood is spread by the spreading layer to migrate through the light-reflecting layer to the reagent layer where it reacts with the reagent system to develop or change the color. After incubating the multi-layered analysis element at a predetermined temperature for a predetermined time period, the density of the developed color or the degree of color change is determined by optically measuring the reflected light, and then the quantity or content of the analyte contained in the liquid sample is found by using a calibration curve. The light-reflecting layer is provided to eliminate the influence of the color of the liquid sample to provide a white background at the time of the optical density measurement operation.

However, in the conventional dry chemical analysis process, it is a common practice to remove red blood cell from the whole blood to prepare blood serum or blood plasma which is used as the sample liquid. Cumbersome and time-consuming operations and a specially designed device are needed for the red blood cell of erythrocyte from the whole blood. Accordingly, in order to realize rapid and simple operation, there is an increasing demand for the provision of a dry process in which the whole blood can be used as the sample liquid without any preparatory operation.

PRIOR ART

Japanese Patent Publication No. 21677/1978 (corresponding to U.S. Pat. No. 3,992,158), Unexamined Japanese Patent Publication No. 111960/1985 (corresponding to U.S. Pat. No. 4,637,978) and Unexamined Japanese Patent Publication No. 27980/1985 propose dry multi-layered analysis elements using the whole blood as the sample, in which provided are filtering layers for separating blood cells and high molecular weight ingredients such as proteins materials in the blood.

The filtering layers proposed by the preceding patents are made of a porous polymer membrane (membrane filter), such as a cellulose acetate membrane, or a porous layer having continuous pores formed by micro particles so that the blood cell components are trapped to at the surface or at the vicinity of the surface of the filter layer to be removed from the liquid sample. Accordingly, in order to remove the blood cells to sufficient extent, it is necessary to use a filter material having sufficiently small pore size. However, as the pore size becomes smaller, the time required for passing the blood plasma is prolonged to inhibit rapid measurement. In addition, small pore size induces hemolysis leading to increase in optical density of the background due to the presence of hemoglobin pigment, or induces leakage of components in the blood cells to adversely affect the coloring reaction in the detection layer, whereby the results of measurement are scattered to lower the reproducibility of the measurement.

On the other hand, it is known that the glass fiber filter is high in its cell/plasma separating function for separating blood cells from blood plasma in the whole blood, and analysis elements utilizing such a glass fiber filter have been proposed, for example, by Unexamined Japanese Patent Publication Nos. 53661/1982 (corresponding to EP 0 045 476A) and 96466/1986 (corresponding to EP 0 159 727A).

Although these known analysis elements are improved in that hemolysis is suppressed to a small degree, care must be paid at the step of preparing these analysis elements since brittle glass fibers are used, leading to a problem that the production efficiency thereof is lowered. In addition, since the glass fiber filter (or the glass fiber layer) is simply placed on the detection reagent layer or spreading layer, the adhesive strength between the glass fiber layer and the detection reagent layer or spreading layer is low to have a tendency that the glass fiber layer is easily exfoliated from the detection reagent layer or spreading layer. If such exfoliation occurs, the volume of the blood plasma passed to the detection reagent layer is scattered to result in poor reproducibility of the result of measurement.

OBJECTS AND SUMMARY OF THE INVENTION

Accordingly, the object of this invention is to provide a dry analysis element for the quantitative analysis of an analyte contained in whole blood, which is easily produced to be used as an analysis element on which whole blood can be spotted directly as the sample liquid to give quickly a result of quantitative analysis of an analyte contained in the whole blood with high reproducibility.

The aforementioned object has been achieved by the provision of a dry analysis element for the quantitative analysis of an analyte contained in whole blood, comprising a cloth selected from a micro-fibrous cloth made of fibers having an average fiber diameter of from 0.1 to 10 µm, or a napped cloth, each having an average diameter of from 1 to 30 µm; and a detection layer laminated with said microfibrous cloth.

Throughout the specification and appended claims, the term "micro-fibrous cloth" is used to include cloths made of fibers having an average diameter of from 0.1 to 10 µm, the micro-fibrous cloths being in the form of woven fabrics, knitted fabrics, non-woven cloths and napped cloths (napped from any of wove, knitted or non-woven cloths). It should, however, be noted here that when a micro-fibrous cloth is used in the knitted form or texture, the average fiber diameter is extended to include the additional range of from 10 to 30 µm. The material for the micro-fibrous cloths and napped fabrics is not limited, any known natural or synthetic fiber materials may be used.

A porous layer may be interposed between the micro-fibrous or rapped (or pile) fabric and the detection layer.

The present invention is accomplished in view of the finding that the blood cells and blood plasma are separated without hemolysis when a cloth of special construction, that is the micro-fibrous cloth (a woven fabric, knitted fabric, napped fabric and non-woven cloth) or napped fabric as defined in the appended claims, is used. In other words, the present invention utilizes the special blood cells/blood plasma separation function of these micro-fibrous cloths or napped fabric.

Although the separation function has not been fully clarified, it is estimated that the blood cells are trapped not only by the surface of each of these cloths but also they are trapped by a so-called volume filtration function by which blood cells are trapped to be removed along the whole thickness direction of the cloth. In detail, as the blood moves along the thickness direction of the used cloth or fabric, large blood cells are initially trapped by the fibrous construction and then smaller blood cells are trapped.

The porous layer provided in the preferred embodiment serves as a spreading layer. However, since each of the micro-fibrous cloth and napped fabric used in accordance with this invention exhibits a spreading function of some extent, the porous layer need not be provided so that the used cloth serves as a layer for effecting both of the cell separation function and the spreading function.

DESCRIPTION OF APPENDED DRAWING

The sole FIGURE, FIG. 1, appended to the specification schematically illustrates a pattern of spot-bonding.

DESCRIPTION OF PREFERRED EMBODIMENT

The dry analysis element of this invention is essentially the microfibrous cloth (a woven fabric, knitted fabric, napped fabric and non-woven cloth) and a detection layer laminated with the cloth. A porous layer may be interposed between the cloth and the detection layer. The analysis element of this invention may be applied on a transparent support. The detection layer includes at least one reagent layer. The reagent layer may serve also as a detection layer, or the coloring material formed by the coloring reaction may be passed to a separate detection layer for easy detection. The constitutional elements of the dry analysis element of this invention will now be described in detail.

Non-woven Micro-fibrous Cloth

The material for the non-woven microfiber cloth is not particularly limited. It is understood that the function of separating the blood cells from the whole blood does not depend on the chemical properties of the used fibers but depends on the fibrous construction of the non-woven cloth. Accordingly, the object of this invention, i.e. satisfactory separation of blood cells from blood plasma, is achieved by properly selecting the density of the non-woven cloth and the diameter of the fibers forming the non-woven cloth. It is generally desirous that the density of the non-woven cloth ranges from 0.01 to 0.2 $g/cm^3$ and the average fiber diameter ranges from 0.2 to 10 µm.

The used fibers forming the non-woven cloth have an average fiber diameter of from about 0.2 µm to about 10 µm, preferably from about 0.5 µm to about 5 µm. The non-woven cloth has a density of from about 0.01 $g/cm^3$ to about 0.2 $g/cm^3$, preferably from about 0.02 $g/cm^3$ to about 0.1 $g/cm^3$, and a thickness of from about 100 µm to about 2000 µm, preferably from about 150 µm to about 1000 µm, the porosity of the non-woven cloth ranging from about 75% to about 99.5%, preferably from about 85% to, about 98%.

The non-woven cloth may be prepared by any of the known dry processes, such as the spun lase process, the spun bond process, the melt blown method, the needle punch process or the binder process, and the conventional wet processes. It is preferred that a non-woven cloth made of microfibers is prepared by the spun bond process in which microfibers are initially spun and then the thus spun microfibers are bonded to form a non-woven cloth, or by the melt blown process in which a non-woven cloth is prepared directly from a starting material.

Any fibrous materials may be used for the starting material in the spun bond process. Microfibers may be formed by direct spinning (by which microfibers are spun directly), by splitting (by which a composite spun string composed of multiple constituents is splitted to obtain microfibers) or by extraction (by which a composite spun string composed of multiple constituents is subjected to extraction for removing some constituent to obtain microfibers).

Any polymers which can be spun by melt spinning may be used as the starting material for the preparation of a non-woven cloth through the melt blow process. Examples of usable polymer include polyethylene terephthalate (commonly referred to as "polyester"), polybutylene terephthalate, polyethylene, polypropylene and nylon.

Napped (Pile) Fabric

The material for the production of napped (pile) cloth is not particularly limited. Similar to the non-woven cloth, the function of separation of the whole blood into the blood cells and the blood plasma does not depend on the chemical properties of the used fibers but depends on the construction of the napped cloth. Accordingly, the object of this invention, i.e. satisfactory separating the blood cells from the whole blood, is achieved by properly selecting the density of the napped cloth and the diameter and the average length of the fibers forming the napped cloth. It is generally desirous that the fibers have an average fiber diameter of from 1 to 30 µm, that the density of fibers per cm² of the napped cloth ranges from 7.0×10³ to 8.2×10⁶, and that the naps have an average length of from 0.5 to 5.0 mm.

The fibers forming the napped cloth have an average fiber diameter of from about 1 µm to about 30 µm, preferably from about 2 µm to about 20 µm. The density of the napped cloth ranges from about 0.02 g/cm³ to about 1.0 g/cm, preferably from about 0.05 g/cm³ to about 0.7 g/cm³. The thickness of the napped cloth ranges from about 100 µm to about 2000 µm, preferably from about 150 µm to about 1000 µm. The porosity of the napped cloth ranges from about 45% to about 70%, preferably from about 50% to about 65%.

The napped cloth is not limited to those made of fibers (referred to herein as "micro-fibrous fibers") having an average diameter of not more than 10 µm, but natural vegetable fibers, such as cotton and linen, and animal fibers, such as wool, Kashmir and silk, having an average diameter of generally from 10 to 30 µm may also be used as the materials for the napped cloth within the scope of the invention.

Specific examples of the napped cloth which may be conveniently used in the invention will be set forth below.

(1) Napped fabrics prepared by napping or piling woven cloths, the examples being velvet, velveten, velour, etc.;

(2) Napped fabrics prepared by napping or piling knitted cloths, the examples being ribbed fabric velour, double raschel fabric velour, tricot fabric velour, etc.; and (3) Napped non-woven cloths.

It is preferred that the volume of spotted whole blood is controlled such that the interrelationship between the average nap length L (in µm unit) and the volume V (in µl unit) of spotted whole blood is maintained within the following range of:

$$5 \leq L/V \leq 200.$$

Micro-fibrous Cloth

The material for the production of micro-fibrous cloth is not particularly limited. It is understood that the function of separating the blood cells from the blood plasma does not depend on the chemical properties of the used fibers but depends on the physical construction of the cloth. Accordingly, the object of-this invention, i.e. satisfactory separation of blood cells from whole blood, is achieved by properly selecting the density of the cloth and the diameter of the filaments forming the cloth. It is generally desirous that the filaments have an average filament diameter of from 0.1 to 7 µm, and that the porosity of the cloth ranges from 45 to 70%.

The filaments forming the cloth have an average filament diameter of from about 0.1 µm to about 7µm, preferably from about 0.2 µm to about 7.0 µm. The density of the cloth ranges from about 0.02 g/cm³ to about 1.0 g/cm³, preferably from 0.05 g/cm³ to about 0.7 g/cm³. The thickness of the cloth ranges from about 100 µm to about 2000 µm, preferably from about 150 µm to about 1000 µm. The porosity of the cloth ranges from about 45% to about 70%, preferably from about 50% to about 65%.

Provided that the aforementioned conditions are satisfied, micro-fibrous cloths may be used in various forms including, for example, woven fabrics and knitted fabrics.

The cross-section of each filament is not limited to circular, but the filament may have elipitical, triangular, square, star-shaped or any other modified cross-section fiber. The average diameter of the filaments may be calculated from the following equation of:

$$\text{Average Diameter} = 2 \times (S/\pi)^{0.5}$$

wherein S is an average area of the cross section of the filaments.

Specific examples of micro-fibrous cloth include a direct-spun micro-fibrous cloth, a splitted micro-fibrous cloth and an extracted micro-fibrous cloth. The direct-spun micro-fibrous cloth is a cloth prepared from microfibers which are spun directly from a starting material. The splitted micro-fibrous cloth is a cloth prepared from composite spun strings each composed of multiple constituents, followed by splitting the composite spun strings by a proper processing (for example, by thermal or physical processing or by treating with a proper solvent) to form a cloth made of microfilaments. The extracted micro-fibrous cloth is a cloth prepared from composite spun strings each composed of multiple constituents, followed by extracting some constituent with a proper solvent to form a cloth made of microfilaments.

All of the aforementioned micro-fibrous cloths and napped fabric have the so-called volume filtration function. Accordingly, for the simplicity of description, these cloths will be referred to as "the volume filtering layer" in the following description.

Porous Layer

The porous layer is a layer for spreading the plasma separated from the blood cells by the volume filtering layer to feed the thus separated plasma to the detection layer laminated beneath the porous layer. The porous layer is a layer separated from the volume filtering layer and may be made of a fibrous material or non-fibrous material.

When the porous layer is made of a fibrous material, the layer may be made of filter paper, a non-woven cloth, a woven cloth (such as a plain weave), or a knitted cloth (such as a tricot knitted cloth). The woven and knitted cloths are preferably used. The used woven or knitted cloth may be subjected to the glow discharge treatment as described in Unexamined Japanese Patent Publication No. 66359/1982 (corresponding to U.S. Pat. No. 4,783,315), or may be subjected to the alkali etching treatment for reducing volume by the use of an alkali as described in Japanese Patent Publication Nos. 11709/1984 and 24233/1984.

When the porous layer is made of a non-fibrous material, it is preferred that the layer is a blush polymer layer (membrane filter) made of cellulose esters, such as cellulose acetate, cellulose acetate butyrate and cellulose nitrate, as described in Japanese Patent Publication No. 21677/1978 (corresponding to U.S. Pat. No. 3,992,158) and U.S. Pat. No. 1,421,341. Porous membranes each having micropores and made of a polyamide, such as 6-nylon or 6,6-nylon, a polyethylene or a polypropylene may also be used. A further example of usable porous layer is a porous membrane having micropores and made of a polysulfone as disclosed by Unexamined Japanese Patent Publication No. 27006/1987. Still further examples of usable porous layer are disclosed by Japanese Patent Publication No. 21677/1978 and Unexamined Japanese Patent Publication No. 90859/1980 (corresponding to U.S. Pat. No. 4,258,001), which are made of fine particles of a polymer, glass or diatomaceous earth bound with each other by spot-bonding with a hydrophilic or non-water-absorptive polymer to have continuous pores.

When the volume filtrating layer exhibits the spreading function, the multi-layered analysis element of this invention may be prepared without the provision of this porous layer. However, in a preferred embodiment of the invention, the volume filtrating layer is laminated with this porous layer and partially bound together, for example by spot-bonding, to form an integral porous construction which serves to separate the blood cells, to spread the blood plasma (to effect the metering function) and to feed the thus separated blood plasma onto the detection layer laminated below the integral porous construction.

It is preferable that the porous layer contains a hydrophilic polymer or a surface active agent selected from those as set forth below, in order that the spreading function thereof is uniformalized.

(1) Hydrophilic Polymer

Hydrophilic cellulose derivatives as disclosed in Unexamined Japanese Patent Publication No. 222770/1985 (corresponding to EP 0 162 301A);

Methyl cellulose, ethyl cellulose and polyvinyl alcohol as disclosed in Unexamined Japanese Patent Publication No. 21533/1988 (corresponding to EP 0 254 202A);

Polyvinyl pyrrolidone;

Polyacrylates;

Hydrophilic polymers as disclosed in Unexamined Japanese Patent Publication No. 182652/1987 (corresponding to DE 37 17 913A) including homopolymers and copolymers of acrylamide and N-substituted or N,N-disubstituted acrylamide.

(2) Surface Active Agent

Nonionic surface active agents, such as nonylphenoxy polyethoxyethanol, as disclosed in Japanese Patent publication No. 21677/1978 (corresponding to U.S. Pat. No. 3,992,158) and Unexamined Japanese Patent Publication No. 164356/1980 (corresponding to U.S. Pat. No. 4,292,272);

Nonionic surface active agents each having an HLB value of not less than 10, as disclosed in Unexamined Japanese Patent Publication No. 222770/1985 (corresponding to EP 0162 301A);

Nonionic surface active agents, such as polyhydric alcohol ester ethylene oxide adducts, polyethylene glycol fatty acid esters, higher alcohol ethylene oxide adducts, alkylene phenol ethylene oxide adducts, and higher fatty acid alkanolamides as disclosed in Unexamined Japanese Patent Publication No. 21533/1988 (corresponding to EP 0 254 202A); and Fluorine-containing surface active agents as disclosed in Unexamined Japanese Patent Publication No. 6167/1987 (Cemical Abstracts, 107, 171961w) and Unexamined Japanese Patent Publication No. 196849/1988 (corresponding to EP 0278 496A).

These hydrophilic polymers and surface active agents may be used singly or in combination.

When the volume filtrating layer is utilized as a layer exhibiting the spreading function, it is desirous that any one or more of the hydrophilic polymers and/or surface active agents is contained in the volume filtrating layer in both of the case where a porous layer is not provided and the case where a porous layer is provided.

Detection Layer

The detection layer is a layer for receiving the blood plasma through the porous layer (or directly from the volume filtrating layer) to serve as a layer for detecting the analyte. The detection layer comprises at least one reagent layer where a coloring (or color-changing) reaction takes place and then the color density is detected. In a modified embodiment, the detection layer comprises a reagent layer where a coloring (or color-changing) reaction takes place, and a separate detection layer for receiving the pigment formed in the reagent layer to detect the quantity or content of the thus formed pigment.

Reagent Layer

The reagent layer contains a reagent composition which is colored or changed in color or absorption spectrum within the range of ultraviolet rays in the presence of the analyte, the developed color, color change or change of UV absorption spectrum being detectable by optical means. The reagent layer comprises a water-permeable layer made of a hydrophilic polymer binder or a porous layer, and contains a reagent composition.

(1) In case where the reagent layer comprises a water-permeable layer made of a hydrophilic polymer binder:

Examples of hydrophilic polymer binders which may be used in the present invention include gelatine and derivatives thereof such as phthalated gelatine; derivatives of cellulose such as hydroxyethyl cellulose; agarose; polyacrylamides, polymethacrylamides, and copolymers of acrylamides or methacrylamides with various vinyl monomers; polyvinyl alcohol; and polyvinyl pyrrolidone. All of the components forming the reagent composition may be contained in the hydrophilic polymer binder, or some one or more components of the reagent composition may be contained in the hydrophilic polymer binder with the remaining components being contained in another layer. These components should be contained in the hydrophilic polymer binder substantially uniformly.

The reagent layer having a hydrophilic polymer as the binder may be formed, for example, by the methods disclosed in Japanese Patent Publication No. 21667/1978 (corresponding to U.S. Pat. No. 3,992,158), Unexamined Japanese Patent Publication No. 164356/1980 (corresponding to U.S. Pat. No. 4,292,272), Unexamined Japanese Patent Publication No. 101398/1979 (corresponding to U.S. Pat. No. 4,132,528) Unexamined Japanese Patent Publication No. 292063/1986 and (Chemical Abstracts, 106, 210567y). In detail, an aqueous solution or dispersion containing a reagent composition and a hydrophilic polymer is applied on another layer, e.g. a support or a detection layer, followed by drying. The thickness of the reagent layer made of a hydrophilic polymer binder at the dry state ranges generally from about 3 μm to about 50 μm, preferably from about 5 μm to about 30 μm, and the coverage thereof ranges generally from about 3 g/m$^2$ to about 50 g/m$^2$, preferably from about 5 g/m$^2$ to about 30 g/m$^2$.

(2) In case where the reagent layer comprises a porous layer containing a reagent composition (porous reagent layer):

Such a porous reagent layer may comprise a porous layer which is similar to that described hereinbefore, or a porous construction made of solid micro particles bonded by a polymer binder. The latter-mentioned construction is disclosed in Unexamined Japanese Patent Publication No. 120957/1984 (corresponding to EP 0 114 403A).

A reagent composition may be contained in such a porous reagent layer by impregnation or application of a solution or dispersion of the reagent composition. The porous reagent layer containing the reagent composition is laminated on another water-permeable layer, for example, a second reagent layer, a water-absorbing layer, a detection layer or an adhesive layer. Lamination of the porous reagent layer may be effected, as disclosed in Unexamined Japanese Patent Publication No. 164356/1980 (corresponding to U.S. Pat. No. 4,292,272), by pressing the porous reagent layer with a light pressure on an underlying layer which is uniformly wetted with water.

Alternatively, after laminating a porous layer on a water-absorbing layer, a detection layer or an adhesive layer by the process as disclosed in Unexamined Japanese Patent Publication No. 164356/1980 (corresponding to U.S. Pat. No. 4,292,272), a solution or dispersion of a reagent composition may be applied over the porous layer to form a porous reagent layer.

Impregnation or application of a solution of a reagent composition into the porous reagent layer may be effected by any known method. For example, a solution of a reagent composition may be applied by dip coating, doctor coating, hopper coating or curtain coating.

(3) Reagent Composition

Any reagent composition may be used provided that it forms an optically detectable substance (e.g. a pigment or dye) in the presence of the analyte. The reagent composition may be the one which reacts directly with the analyte to be colored or to be changed in color; or it may be a composition or indicator which forms an optically detectable substance (e.g. a pigment or dye) by reacting with an intermediate formed by the reaction between the analyte and another reagent (for example, a reagent composition containing an enzyme as disclosed in Unexamined Japanese Patent Publication No. 138756/1987 (corresponding to EP 0 226 465A)). Specific examples of the reagent composition which may be used in the present invention will be set forth below.

(i) A composition forming a pigment by the oxidation of a leuco dye, such as triarylimidazol leuco dye as disclosed in U.S. Pat. No. 4,089,747 and diarylimidazol leuco dye as disclosed in Unexamined Japanese Patent Publication No. 193352/1984 (corresponding to EP 0 122 641A);

(ii) Diazonium salts (iii) A composition containing a compound which couples with another compound upon oxidation, such as combinations of 4-aminoantipyrines with phenols or naphthols;

(iv) A compound which forms a pigment in the presence of a reduced co-enzyme and an electron transferring agent.

When the analysis element is used for determining the enzyme activity, the reagent layer or the porous layer may contain an auto color developing substrate which can release a colored substance such as p-nitrophenol.

The reagent composition may contain, if necessary, an activator, a buffer reagent, a membrane hardener or a surface active agent. Examples of the buffer reagent which may be contained in the reagent layer in this invention include carbonates, borates, phosphates and Good's buffer reagent disclosed in "Biochemistry", vol. 5, pages 467 to 477 (1966). A proper buffer reagent may be selected from those disclosed in "TANPAKUSHITU KOSO NO KISOJIKKEN-HO" ("Fundamental Experiment Methods Relating to Proteins and Enzymes"), written by Takeichi HORIO et al and published by NANKODO in 1981 and "Biochemistry", vol 5, pages 467 to 477 (1966).

When the coloring reaction takes place through multiple reaction stages, the reagent layer may be divided into two or more layers so that corresponding components of the reagent composition are contained in respective layers.

Detection Layer

The detection layer receives the dye or other optically detectable product formed in the reagent layer in the presence of the analyte. The optically detectable product or dye passed to the detection layer is measured by optical means through a transparent support. The detection layer may comprise a hydrophilic polymer.

The detection layer may contain, as desired, a mordant to facilitate easy detection of the coloring material, a specific example of the mordant being a cationic polymer which is a mordant for an anionic dye.

A water-absorbing layer may be provided below the detection layer. The water-absorbing layer absorbs water to develop a negative diffusing pressure to accelerate diffusion and impregnation of the blood plasma into the porous layer or the reagent layer and to accelerate migration of the dye into the detection layer while preventing the dye formed in the reagent layer from diffusing or spreading into the water-absorbing layer per se. Such a water-absorbing layer may comprise a hydrophilic polymer which is easily swelled with water.

A light-shielding layer may be provided above the detection layer and at least below the volume filtrating or porous layer. The light-shielding layer shields red color of hemoglobin contained in erythrocyte at the step of measuring the reflected light from the transparent support side to find the detectable change (e.g. a color change or color density) occurred in the detection layer or the reagent layer, and additionally acts as a light reflecting layer or a background layer. The light-shielding layer may be a layer composed of a hydrophilic binder containing light reflecting fine particles of, for example, titanium dioxide or barium sulfate, or may be a porous layer containing light reflecting fine particles.

Support

An example of preferable material for the support is polyethylene terephthalate. Cellulose esters, such as cellulose triacetate, polystyrene and polycarbonate prepared from bisphenol A may also be used as the material for the support. The support is generally light-transmitting (transparent) and water-impermeable. However, a water-permeable or water-passing support or a light-shielding (opaque) support may also be used. The support is usually applied with an undercoating layer or subjected to hydrophilization treatment so that it is firmly adhered to the hydrophilic layer laminated thereon.

However, the support need not be provided when the volume filtrating layer constituted of of a non-woven microfibrous cloth or a napped cloth has a physical strength high enough for retaining the construction of the analysis element.

Overall Construction of Analysis Element

The analysis element of this invention may have a manifold construction. The construction of the analysis element may be modified similar to the layer constructions of various multi-layered analysis elements disclosed in Unexamined Japanese Patent Publication No. 53888/1974 (corresponding to U.S. Pat. No. 3,992,158), Unexamined Japanese Patent Publication No. 164356/1980 (corresponding to U.S. Pat. No. 4,292,272), Unexamined Japanese Patent Publication No. 222769/1985 (corresponding to EP 0 162 302A), Unexamined Japanese Patent Publication Nos. 138756/1987 to 138758/1987 (corresponding to EP 0 226 465A). As has been described hereinbefore, the porous layer is not provided in one embodiment of this invention.

Examples of the construction adapted for practical use will be set forth below.

(1) A construction composed of a support, a reagent layer containing a hydrophilic polymer binder and laminated on the support, and a volume filtrating layer laminated on the reagent layer;

(2) A construction composed of a support, a reagent layer containing a hydrophilic polymer binder and laminated on the support, a porous layer laminated on the reagent layer, and a volume filtrating layer laminated on the porous layer;

(3) A construction composed of a support, a water-absorbing layer laminated on the support, a reagent layer containing a hydrophilic polymer binder and laminated on the water-absorbing layer, a porous layer laminated on the reagent layer, and a volume filtrating layer laminated on the porous layer;

(4) A construction composed of a support, a detection layer laminated on the support, a reagent layer containing a hydrophilic polymer binder and laminated on the detection layer, a porous layer laminated on the reagent layer, and a volume filtrating layer laminated on the porous layer;

(5) A construction composed of a support, a water-absorbing layer laminated on the support, a porous layer containing a reagent composition and laminated on the water-absorbing layer, and a volume filtrating layer laminated on the porous layer; and (6) A construction composed of a support, a detection layer laminated on the support, a porous layer containing a reagent composition and laminated on the detection layer, and a volume filtrating layer laminated on the porous layer.

The support may be applied with an undercoating layer.

Partial Adhesion (Spot-Bonding)

The partial adhesion or spot-bonding between the volume filtrating layer and the porous layer or detection layer, which is a further characteristic feature of the multi-layered analysis element of this invention, will now be described.

The terminology "partial adhesion" as used herein is a definition of the adhesion feature or mode between adjacent porous layers or between a porous layer and an adjacent non-porous layer, and means "an adhesion at the interface between adjacent two layers which are bonded substantially intimately to form an integral structure by adhesion spots arranged partially or discontinuously on the interface so as not to hinder substantially uniform passage of a liquid through and between the adjacent two layers" as defined in Unexamined Japanese Patent Publication No. 4959/1986 (corresponding to EP 0 166 365A) and Unexamined Japanese Patent Publication Nos. 138756/1987 to 138758/1987 (corresponding to EP 0 226 465A). In the multi-layered analysis element of this invention, the interface between the volume filtrating layer and the adjacent porous layer or the interface between the volume filtrating layer and the adjacent detection layer is partially adhered with each other.

Usually, an adhesive is spotted partially on the volume filtrating layer, and then the porous layer or the detection layer is applied thereon by pressing the latter with a light pressure. Alternatively, an adhesive may be spotted partially on the porous layer or the detection layer and then the porous layer or the detection layer is placed on the volume filtrating layer to be bonded together by pressing with a light pressure. An adhesive may be spotted partially on the volume filtrating layer, and then a porous sheet material for forming the porous layer is applied thereon by uniformly pressing with a light pressure. Otherwise, an adhesive may be spotted partially on a porous sheet material forming the porous layer and applied on the volume filtrating layer by uniformly pressing with a light pressure, and then the detection layer is applied on the porous sheet material.

An adhesive may be spotted or partially applied on the volume filtrating layer, the porous layer or the detection layer by any of the processes as disclosed in Unexamined Japanese Patent Publication No. 4959/1986 (corresponding to EP 0 166 365A), Unexamined Japanese Patent Publication No. 138756/1987 (corresponding to EP 0 226 465A), Unexamined Japanese Patent Publication No. 23160/1989 (corresponding to DE 37 21 236A). A printing process is preferred than other processes. The process for applying an adhesive by transferring the adhesive from a printing roller (preferably a gravure or intaglio printing roller) and the process for binding two adjacent layers may be effected by using a known apparatus and method as disclosed, for example, in "INSATSU KOGAGU BINRAN" ("Handbook of Printing Technology"), edited by NIPPON INSATSU GAKKAI and published by GIHODO SHUPPAN K. K. in 1983, pages 838 to 858.

Known adhesives disclosed in Unexamined Japanese Patent Publication No. 138756/1987 (corresponding to EP 0 226 465A) and on pages 839 to 853 of the "INSATSU KOGAGU BINRAN" referred to above may be used. Examples of adhesive which may be used in the present invention include water-soluble adhesives, adhesives soluble in organic solvents and thermally thermoplastic or thermosetting adhesives (hot-melt type and heat sensitive adhesives). Specific examples of the water-soluble adhesive are aqueous adhesives such as starch, aqueous solutions of dextrin, carboxymethyl cellulose and polyvinyl alcohols, and emulsion of copolymer of vinyl acetate and butyl acrylate. It is preferred to use an adhesive soluble in an organic solvent which is vaporized relatively slowly. The thermoplastic or thermosetting adhesives (hot-melt type or heat sensitive adhesives) are particularly preferable.

The hot-melt type adhesives disclosed in "KOGYO ZAIRYO" ("Industrial Materials"), vol. 26, No. 11, pages 4 to 5, may be used. Specific examples of the hot-melt type adhesive are copolymers of ethylene, such as ethylene/vinyl acetate copolymer, ethylene/ethyl acrylate copolymer, ethylene/acrylic acid copolymer; polyolefins such as low molecular weight polyethylene and atactic polypropylene; polyamides such as nylon; polyester copolymers; thermoplastic rubbers such as SBS or other block copolymers of styrene; styrene-butadiene rubber, butyl rubber and urethane rubber; rosin, petroleum resins and terpentine resins; and synthetic rubbers.

EXAMPLES

The present invention will now be described by referring to some Examples and Comparative Examples to facilitate full understanding of the invention.

Example 1 and Comparative Example 1

Preparation of an integral multi-layered analysis element for the quantitative analysis of glucose An analysis element A was prepared by laminating a support, a reagent layer, a light-shielding layer and a non-woven cloth successively in this order.

Initially, an aqueous solution of a reagent composition was coated over the surface of a 180 μm thick, colorless, transparent polyethylene terephthalate (PET) sheet serving as a support, followed by drying, to form a reagent layer having a coverage as set forth below.

Coverage (per 1 m$^2$) of the Reagent Layer

| | |
|---|---|
| Deionized Gelatine | 26 g |
| Glucose Oxidase | 2000 U |
| Peroxidase | 3300 U |
| 4-[4-(Dimethylamino)phenyl]-5-phenetylimidazol (Leuco Dye) Acetate | 1600 mg |
| 1,7-Dihydroxynaphthalene | 660 mg |
| Nonylphenoxypolyethoxyethanol (Average Content of Oxyethylene unit: 10) | 270 mg |

An aqueous dispersion having the following composition was coated on the reagent layer to form a light-shielding layer (Thickness at the Dry State: about 7 μm) having a coverage as set forth below.

Coverage of Light-Shielding Layer (Per 1 m²)

| | |
|---|---|
| Deionized Gelatine | 2.9 g |
| Fine Particle of Rutile type Titanium Dioxide | 13 g |
| Nonylphenoxypolyethoxyethanol (Average Content of Oxyethylene unit: 10) | 600 mg |

The surface of the light-shielding layer was uniformly wetted with water, and a polyester melt-blown type non-woven cloth (Average Fiber Diameter: 0.8 μm, Density: 0.13 g/cm³, Thickness: about 400 μm) was placed on the wetted light-shielding layer followed by pressing evenly with a light pressure. Then the laminate was dried to form an integral construction.

A 20 wt % solution of polyvinyl pyrrolidone (Average Molecular Weight: 360,000) in ethanol was coated on the non-woven cloth and dried to have a coverage at the dry state of 4 g/m², whereby an integral multi-layered analysis element (Element A) was prepared.

As a Comparative Example, an integral multi-layered analysis element (Element B) was prepared similar to Element A except that a cellulose acetate membrane filter having a nominal pore size (i.e. the effective pore size or the average value of smallest pore size) of 1.2 μm, a thickness of about 140 μm and a porosity of about 80% was used in place of the polyester non-woven cloth.

On each of the Elements A and B spotted was 20 μl of normal human whole blood (Hematocrit Value: 42%, Glucose content in the Blood Plasma: 122 mg/ml). Each element was incubated at 37° C. for 6 minutes, and immediately after incubation, the absorbency of the reflected light in the element was measured from the support side using visible lights having center wavelengths of 540 nm and 640 nm. Ten samples were used for each element to repeat the measurement for ten times, and the average value and the standard deviation (SD) of the results of repeated measurement were calculated. The results are shown in Table 1.

TABLE 1

| | 540 nm | | 640 nm | |
|---|---|---|---|---|
| | Element A | Element B | Element A | Element B |
| 1 | 0.087 | 0.450 | 1.121 | 0.730 |
| 2 | 0.088 | 0.524 | 1.121 | 0.730 |
| 3 | 0.090 | 0.398 | 1.119 | 0.745 |
| 4 | 0.086 | 0.440 | 1.120 | 0.721 |
| 5 | 0.090 | 0.501 | 1.120 | 0.721 |
| 6 | 0.088 | 0.485 | 1.120 | 0.735 |
| 7 | 0.088 | 0.487 | 1.122 | 0.711 |
| 8 | 0.089 | 0.296 | 1.119 | 0.769 |
| 9 | 0.088 | 0.456 | 1.115 | 0.800 |
| 10 | 0.087 | 0.533 | 1.116 | 0.798 |
| Average | 0.0881 | 0.4570 | 1.1176 | 0.7622 |
| SD | 0.0012 | 0.0660 | 0.0035 | 0.0362 |

The absorbancy of the reflected light at 540 nm, i.e. the absorbance by hemoglobin contained in the erythrocyte, was substantially negligible in the Element A in which the non-woven micro-fibrous cloth was used. On the contrary, the absorbency of the reflected light at 540 nm in the Element B or Comparative Example was relatively high as about 0.46, which revealed that separation of blood cells was insufficient or hemolysis occurred in the Element B. In contrast thereto, red blood cells were removed substantially completely and hemolysis did not take place in the Element A in which the non-woven cloth was used.

On the other hand, the absorbency of the reflected light at 640 nm, i.e. the absorbance corresponding to the content or concentration of glucose in the blood plasma, was relatively high as 1.118 in the Element A, with insignificant scattering of the measured data (SD=0.004). On the contrary, the absorbency of the reflected light at 640 nm was lowered to 0.762 in the Element B, with significant scattering of the measured data (SD=0.036). The result showed that hemolysis occurred in the Element B to inhibit dye forming reaction.

The element A prepared by the present invention exhibits improved cell separation function and improved resistance to hemolysis. It is also excellent in sensitivity and reproducibility at the measuring step.

Example 2 and Comparative Example 2

Preparation of an integral multi-layered analysis element for the quantitative analysis of total bilirubin An analysis element C was prepared by laminating a support, a first water-absorbing layer, a second water-absorbing layer, a reagent layer, and a non-woven cloth successively in this order.

Initially, an aqueous solution of a composition forming the first water-absorbing layer (Thickness at the Dry State: about 15 μm) was coated and dried on the surface of a 180 μm thick, colorless, transparent polyethylene terephthalate (PET) sheet serving as a support, and then an aqueous solution of a composition forming the second water-absorbing layer (Thickness at the Dry State: about 10 μm) was coated on the first water-absorbing layer.

Coverage (per 1 m²) of the First Water-Absorbing Layer

| | |
|---|---|
| Polyvinyl Alcohol (Degree of Hydrolysis: 88%, Viscosity of a 4% Aqueous solution at 20° C.: 5 cps.) | 14 g |
| Nonylphenoxypolyglycidol (Average content of Glycidol Unit: 10) | 350 mg |

Coverage (per 1 m²) of the Second Water-Absorbing Layer

| | |
|---|---|
| Polyvinyl Alcohol (Degree of Hydrolysis: 99%, Viscosity of a 4% Aqueous solution at 20° C.: 5 cps.) | 9.4 g |
| Nonylphenoxypolyglycidol (Average content of Glycidol Unit: 10) | 300 mg |

After uniformly wetting the second water-absorbing layer with water, the layer was hydrophilized with an aqueous solution of nonylphenoxypolyglycidol (Average content of Glycidol Unit: 10), and then a dry broad woven cloth made of 100 count twin cotton threads was laminated on the second water-absorbing layer by pressing with a uniform light pressure, whereby a matrix for a porous reagent layer was formed.

A solution of a first reagent composition was coated over the woven cloth to be impregnated thereinto, followed by drying, so that the coverage of the first reagent composition reached the value as set forth below.

Coverage (per 1 m²) of the First Reagent Composition

| | |
|---|---|
| 7-(2,3-Dihyroxypropyl)theophylline (CA Registry No. 479-18-5) | 25 g |
| Sulfosalicylic Acid | 5 g |
| Hydroxypropyl Methacrylate/N-(∝-sulfomethyl-∝-methylethyl)acrylamide (6/4) Copolymer | 2.5 g |
| 2,4-Dichlorobenzenediazonium Sulfosalicylate | 320 mg |

Then, a solution of a second reagent composition was coated over the woven cloth to be impregnated thereinto, followed by drying, so that the coverage of the second reagent composition reached the value as set forth below, whereby a light-shielding layer was formed on the woven cloth (serving as a porous reagent layer).

Coverage (per 1 m²) of the Second Reagent Composition

| | |
|---|---|
| Fine Particle of Titanium Dioxide | 11 g |
| 7-(2,3-Dihyroxypropyl)theophylline | 30 g |
| Nonylphenoxypolyglycdol (Average content of Glycidiol Unit: 10) | 1 g |

A nylon non-woven cloth prepared by the spun bond process and having an average fiber diameter of 3.7 μm, a density of 0.05 g/cm³ and a thickness of about 500 μm was closely placed on the woven cloth (porous reagent layer) to prepare an integral multi-layered analysis element (Element C) for the quantitative analysis of total bilirubin.

As a Comparative Example, an integral multi-layered analysis element (Element D) was prepared similar to Element C except that a cellulose acetate membrane filter having a nominal pore size of 1.2 μm, a thickness of about 140 μm and a porosity of about 80% was used in place of the nylon non-woven cloth.

On each of the elements C and D spotted was 20 μl of normal human whole blood (Hematocrit Value: 42%, Content of Total Bilirubin in the Blood Plasma: 0.98 mg/dl). Each element was incubated at 37° C. for 6 minutes, and immediately after incubation, the absorbency of the reflected light in the element was measured from the support side using visible lights having center wavelengths of 600 nm and 540 nm.

Ten samples were used for each element to repeat the measurement for ten times, and the average value and the standard deviation (SD) of the results of repeated measurement were calculated. The results are shown in Table 2.

TABLE 2

| | 600 nm | | 540 nm | |
|---|---|---|---|---|
| | Element C | Element D | Element C | Element D |
| 1 | 0.613 | 0.354 | 0.885 | 0.980 |
| 2 | 0.620 | 0.384 | 0.890 | 1.038 |
| 3 | 0.617 | 0.333 | 0.888 | 1.002 |
| 4 | 0.618 | 0.366 | 0.900 | 0.991 |
| 5 | 0.613 | 0.320 | 0.892 | 0.978 |
| 6 | 0.619 | 0.347 | 0.896 | 1.012 |
| 7 | 0.616 | 0.399 | 0.870 | 1.008 |
| 8 | 0.618 | 0.411 | 0.895 | 1.169 |
| 9 | 0.617 | 0.322 | 0.889 | 0.992 |
| 10 | 0.620 | 0.334 | 0.877 | 1.008 |
| Average | 0.6171 | 0.3570 | 0.8882 | 1.0178 |
| SD | 0.0024 | 0.0304 | 0.0086 | 0.0530 |

The absorbency of the reflected light at 600 nm, i.e the absorbance by the formed dye, was relatively high as 0.617 with insignificant scattering of the data (SD=0.002) in the Element C. In the Element D, the absorbancy of the reflected light at 600nm was relatively low as 0.357 with significant scattering (SD=0.030). The result revealed that hemolysis occurred in the Element D to inhibit the dye forming reaction.

The absorbency of the reflected light at 540 nm is the sum of the absorbance by the formed dye and the absorbance by the red blood cell. The absorbance at 540 nm was 0.888 in the Element C, and that in the Element D was 1.018 which was higher than the absorbance in the Element C. As seen, in the Element D, the absorbance at 600 nm was low to show that the quantity of the formed dye was small, whereas the absorbance at 540 nm was high. This revealed that the blood cells were separated only insufficiently in the Element D. In contrast thereto, the Element C prepared in accordance with this invention had improved blood cell separation function and improved resistance to hemolysis, and exhibited excellent sensitivity and reproducibility at the measuring step.

Example 3 and Comparative Example 3

Preparation of an integral multi-layered analysis element for the quantitative analysis of total cholesterol An analysis element E was prepared by laminating a support, a first reagent layer (coloring reagent layer), a second reagent layer (porous reagent layer), and a non-woven cloth successively in this order.

Initially, a solution of a coloring reagent composition was coated over the surface of a 180 μm thick, colorless, transparent PET sheet serving as a support, followed by drying, to form a coloring reagent layer (Thickness at the Dry State: about 20 μm) having a coverage as set forth below.

Coverage (per 1 m²) of the Coloring Reagent Layer

| | |
|---|---|
| (Solution of Leuco Dye in Oily Organic Solvent) | |
| 2-(4-Hydroxy-3,5-dimethoxyphenyl)-4-[4-(dimethylamino)phenyl]-5-phenetyl-imidazol (Leuco Dye) Acetate Salt | 415 mg |
| HCl Salt of the Same Leuco Dye | 60 mg |
| N,N-diethyllaurylamide | 7.2 g |
| (Aqueous Solution of Gelatine) | |
| Deionized Gelatine | 22 g |
| Bis [(vinylsulfonylmethylcarbonyl)-amino] methane | 220 mg |

The aqueous solution of gelatine set forth above (Gelatine Content: 15.8 wt %) was stirred in an emulsion forming vessel and added with the solution of the leuco dye in the oily organic solvent as set forth above. The admixture was stirred for about 30 minutes to obtain an emulsion (liquid dispersion of a coloring reagent composition) which was coated on the support and dried to form a coloring reagent layer.

The surface of the coloring reagent layer was then uniformly wetted with water, and a cellulose acetate membrane filter having a nominal pore size (the effective pore size or the average value of minimum pore size) of 1.2 μm, a thickness of about 140 μm and a porosity of about 80% was laminated on the coloring reagent layer while pressing with a uniform light pressure. The laminated coloring reagent layer and the membrane filter were dried to form an integral construction.

Thereafter, an aqueous dispersion of a reagent composition for the determination of cholesterol, the composition being set forth below, was coated on the membrane filter to allow the composition to be impregnated into the membrane filter and then dried to have a coverage as set forth below, whereby a second reagent layer (porous reagent layer) was formed.

Coverage (per 1m²) of the Reagent composition for the Determination of Cholesterol

| | |
|---|---|
| Cholesterol Esterase | 7.7 kU |
| Cholesterol Oxidase | 3.6 kU |
| Lipoprotein Lipase | 5.3 kU |
| Peroxidase | 83 kU |
| Potassium Ferrocyanide | 490 mg |
| Condensation Product of Nonylphenoxy-polyethoxyethanol and Formaldehyde | 400 mg |

On the membrane filter of the laminate bound by spot-bonding was a polypropylene melt-blown type non-woven cloth having an average fiber diameter of 2.6 μm, a density of 0.03 g/cm³ and a thickness of 670 μm, the non-woven cloth being subjected to a glow discharge treatment (Electric Energy: 1.6 kw/m², Oxygen Concentration: 0.1 Torr, 30 seconds) and the spot-bonding being effected by gravure printing process, whereby an integral multi-layered analysis element (Element E) was prepared.

Figure 1:
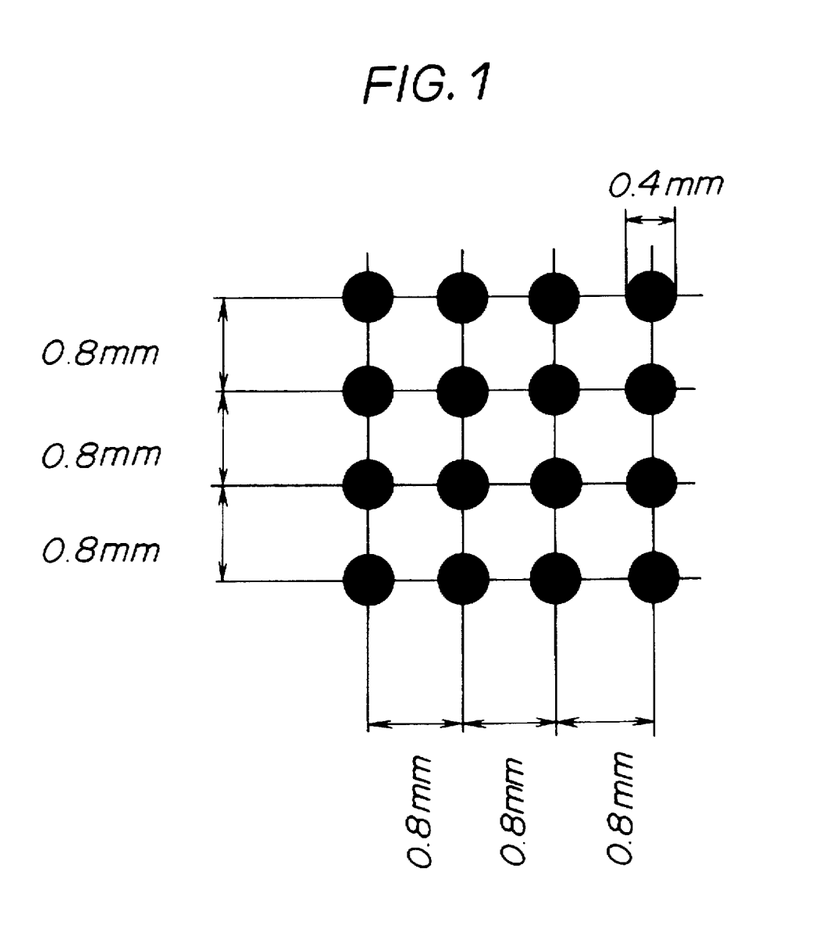

The adhesive used for spot-bonding was a hot-melt type adhesive, Nittaito H6352-2A (produced by Nitta Gelatine K. K.; a styrene/butadiene copolymer having a softening point of 76° C. and a viscosity at 140° C. of 4100 cps.). The adhesive was melted at 135° C., and the molten adhesive was transferred onto the membrane filter using a gravure printing plate having a pattern shown in FIG. 1 (The pattern has circular dots at the cross points of square grating, each dot having a depth of 50 μm, a diameter of 0.4 mm and a shallow U-shaped section, and the lengthwise and lateral distances between the centers of adjacent dots (pitches) being 0.8 mm). Immediately after transferring of the molten adhesive, the membrane filter was pressed to the non-woven cloth to be laminated together.

As a Comparative Example, an integral multi-layered analysis element (Element F) was prepared similar to Element E except that a cellulose acetate membrane filter having a nominal pore size of 1.2 μm, a thickness of about 140 μm and a porosity of about 80% was used in place of the polypropylene non-woven cloth.

On each of the Elements E and F spotted was 20 μl of normal human whole blood (Hematocrit Value: 48%, Content of Total Cholesterol in the Blood Plasma: 151 mg/dl). Each element was incubated at 37° C. for 6 minutes, and immediately after incubation, the absorbency of the reflected light in the element was measured from the polyethylene terephthalate support side using visible lights having center wavelengths of 540 nm and 640 nm.

Ten samples were used for each element to repeat the measurement for ten times, and the average value and the standard deviation (SD) of the results of repeated measurement were calculated. The results are shown in Table 3.

TABLE 3

|  | 540 nm | | 640 nm | |
| --- | --- | --- | --- | --- |
|  | Element E | Element F | Element E | Element F |
| 1 | 0.077 | 0.501 | 1.001 | 0.325 |
| 2 | 0.071 | 0.468 | 1.013 | 0.354 |
| 3 | 0.080 | 0.489 | 0.994 | 0.384 |
| 4 | 0.075 | 0.477 | 0.997 | 0.332 |
| 5 | 0.074 | 0.496 | 1.010 | 0.300 |
| 6 | 0.077 | 0.511 | 1.008 | 0.379 |
| 7 | 0.075 | 0.487 | 0.990 | 0.365 |
| 8 | 0.076 | 0.482 | 1.000 | 0.340 |
| 9 | 0.081 | 0.508 | 1.002 | 0.392 |
| 10 | 0.073 | 0.490 | 1.005 | 0.333 |
| Average | 0.0759 | 0.4909 | 1.0020 | 0.3504 |
| SD | 0.0029 | 0.0128 | 0.0068 | 0.0280 |

The absorbency of the reflected light at 540 nm, i.e the absorbance by erythrocyte, was relatively high as 0.49 in the Element F to show insufficient separation of blood cells. In contrast thereto, the absorbancy of the reflected light in the Element E, in which the non-woven cloth was used, was substantially same as the background level to show that red blood cell was removed substantially completely without significant hemolysis.

The absorbency of the reflected light at 640 nm, i.e. the absorbance by the total cholesterol, was relatively high as 1.00 with insignificant scattering of the measured values (SD=0.007) in the Element E. On the contrary, in the Element F, the absorbency of the reflected at 640 nm was relatively low as 0.35 with significant scattering of the values (SD=0.028). It is understood that hemolysis occurred and the dye forming reaction was inhibited in the Element F.

As seen from the results, the Element E prepared in accordance with the present invention had improved blood cell separation function and improved resistance to hemolysis, and exhibited excellent sensitivity and reproducibility at the measuring step.

Example 4 and Comparative Example 4

Preparation of an integral multi-layered analysis element for the quantitative analysis of glucose An analysis element G was prepared similar to Analysis Element A in Example 1, except that a napped cloth was used in place of the non-woven cloth.

In detail, similar to Example 1, a PET sheet (serving as a support), a reagent layer and a light-shielding layer were laminated successively in this order. The surface of the light-shielding layer was uniformly wetted with water, and a rayon velvet cloth (Average Diameter of Napped Fiber: 15 μm, Fiber Density: 5.5×10⁴/cm², Average Fiber Length: 1.3 mm) was laminated on the light-shielding layer while applying a uniform light pressure so that the ground surface of the velvet cloth was closely fitted on the light-shielding layer. Then, the laminate was dried to form an integral multi-layered analysis element (Element G).

As a Comparative Example, an integral multi-layered analysis element (Element H) was prepared similar to Element G except that a cellulose acetate membrane filter having a nominal pore size (i.e. the effective pore size or the average value of smallest pore size) of 1.2 μm, a thickness of about 140 μm and a porosity of about 80% was used in place of the rayon velvet cloth.

On each of the Elements G and H spotted was 20 μl of normal human whole blood (Hematocrit Value: 42%, Glucose content in the Blood Plasma: 122 mg/ml). Each element was incubated at 37° C. for 6 minutes, and immediately after incubation, the absorbancy of the reflected light in the element was measured from the support side using visible lights having center wavelengths of 540 nm and 640 nm. Ten samples were used for each element to repeat the measurement for ten times, and the average value and the standard deviation (SD) of the results of repeated measurement were calculated. The results are shown in Table 4.

TABLE 4

|  | 540 nm | | 640 nm | |
| --- | --- | --- | --- | --- |
|  | Element G | Element H | Element G | Element H |
| 1 | 0.088 | 0.438 | 1.116 | 0.764 |
| 2 | 0.090 | 0.397 | 1.112 | 0.725 |
| 3 | 0.089 | 0.451 | 1.119 | 0.805 |
| 4 | 0.089 | 0.420 | 1.122 | 0.743 |
| 5 | 0.087 | 0.380 | 1.115 | 0.777 |
| 6 | 0.091 | 0.490 | 1.116 | 0.740 |
| 7 | 0.087 | 0.490 | 1.120 | 0.796 |
| 8 | 0.091 | 0.422 | 1.118 | 0.757 |
| 9 | 0.088 | 0.473 | 1.114 | 0.802 |
| 10 | 0.086 | 0.402 | 1.118 | 0.703 |
| Average | 0.0886 | 0.4317 | 1.1170 | 0.7612 |
| SD | 0.0016 | 0.0451 | 0.0028 | 0.0325 |

The absorbency of the reflected light at 540 nm, i.e. the absorbance by hemoglobin contained in the erythrocyte, was substantially negligible in the Element G in which the napped cloth was used. On the contrary, the absorbency of the reflected light at 540 nm in the Element H of Comparative Example 4 was relatively high as about 0.432, which revealed that separation of blood cells was insufficient or hemolysis occurred in the Element H. In contrast thereto, red blood cells were removed substantially completely and hemolysis did not take place in the Element G in which the napped cloth was used.

On the other hand, the absorbancy of the reflected light at 640 nm, i.e. the absorbance by glucose in the blood plasma, was relatively high as 1.117 in the Element G, with insignificant scattering of the measured data (SD=0.003). On the contrary, the absorbency of the reflected light at 640 nm was lowered to 0.761 in the Element H, with significant scattering of the measured data (SD=0.032). The result showed that hemolysis occurred in the Element H to inhibit dye forming reaction.

The element G prepared by the present invention exhibited improved blood cell separation function and improved resistance to hemolysis. It was also excellent in sensitivity and reproducibility at the measuring step.

Example 5 and Comparative Example 5

Preparation of an integral multi-layered analysis element for the quantitative analysis of total bilirubin An analysis element I was prepared similar to Analysis Element C in Example 2, except that a napped cloth was used in place of the non-woven cloth.

In detail, similar to Example 2, a PET sheet (serving as a support), a first water-absorbing layer, a second water-absorbing layer, and a porous reagent (woven cloth) layer were laminated successively, and a light-shielding layer was provided on the surface of the porous reagent layer.

A nylon tricot velour cloth (Density of Napped Fibers: $3.2 \times 10^4/cm^2$) prepared by knitting nylon strings each having an average fiber diameter of 10 μm to form a tricot pile knitted cloth and then shearing to have a napped fiber length of 800 μm was closely placed on the woven cloth (porous reagent layer) to form an integral multi-layered analysis element (Element I).

As a Comparative Example, an integral multi-layered analysis element (Element J) was prepared similar to Element I except that a cellulose acetate membrane filter having a nominal pore size of 1.2 μm, a thickness of about 140 μm and a porosity of about 80% was used in place of the nylon napped cloth.

On each of the elements I and J spotted was 20 μl of normal human whole blood (Hematocrit Value: 42%, Content of Total Bilirubin in the Blood Plasma: 0.98 mg/dl). Each element was incubated at 37° C. for 6 minutes, and immediately after incubation, the absorbency of the reflected light in the element was measured from the support side using visible lights having center wavelengths of 600 nm and 540 nm.

Ten samples were used for each element to repeat the measurement for ten times, and the average value and the standard deviation (SD) of the results of repeated measurement were calculated. The results are shown in Table 5.

TABLE 5

|  | 600 nm | | 540 nm | |
| --- | --- | --- | --- | --- |
|  | Element I | Element J | Element I | Element J |
| 1 | 0.618 | 0.362 | 0.887 | 0.999 |
| 2 | 0.615 | 0.337 | 0.902 | 1.005 |
| 3 | 0.617 | 0.391 | 0.892 | 1.010 |
| 4 | 0.620 | 0.423 | 0.896 | 1.033 |
| 5 | 0.613 | 0.415 | 0.889 | 1.003 |
| 6 | 0.618 | 0.351 | 0.897 | 0.992 |

TABLE 5-continued

|  | 600 nm | | 540 nm | |
| --- | --- | --- | --- | --- |
|  | Element I | Element J | Element I | Element J |
| 7 | 0.619 | 0.388 | 0.900 | 1.017 |
| 8 | 0.617 | 0.340 | 0.899 | 1.011 |
| 9 | 0.616 | 0.404 | 0.894 | 0.987 |
| 10 | 0.615 | 0.374 | 0.890 | 1.014 |
| Average | 0.6168 | 0.3785 | 0.8946 | 1.0071 |
| SD | 0.0020 | 0.0291 | 0.0048 | 0.0125 |

The absorbancy of the reflected light at 600 nm, i.e the absorbance by the formed dye, was relatively high as 0.617 with insignificant scattering of the data (SD=0.002) in the Element I. In the Element J, the absorbancy of the reflected light at 600 nm was relatively low as 0.379 with significant scattering (SD=0.029). The result revealed that hemolysis occurred in the Element J to inhibit the dye forming reaction.

The absorbancy of the reflected light at 540 nm is the sum of the absorbance by the formed dye and the absorbance by the red blood cell. The absorbance at 540 nm was 0.895 in the Element I, and that in the Element J was 1.007 which was higher than the absorbance in the Element I. As seen, in the Element J, the absorbance at 600 nm was low to show that the quantity of the formed dye was small, whereas the absorbance at 540 nm was high. This revealed that the blood cells were separated only insufficiently in the Element J. In contrast thereto, the Element I prepared in accordance with this invention exhibited improved blood cell separation function and improved resistance to hemolysis, while exhibiting excellent sensitivity and reproducibility at the measuring step.

Example 6 and Comparative Example 6

Preparation of an integral multi-layered analysis element for the quantitative analysis of total cholesterol An analysis element K was prepared similar to Analysis Element E in Example 3, except that a napped cloth was used in place of the non-woven cloth.

In detail, similar to Example 3, a PET sheet (serving as a support), a first reagent layer (coloring reagent layer) and a second reagent layer (porous reagent layer) were laminated successively.

Then, by using the gravure printing process, the back side of a polyester velour cloth prepared by circular knitting and having an average fiber diameter of napped fibers of 5.3 μm, a fiber density of $6.6 \times 10^4/cm^2$ and an average fiber length of 2.5 mm was fitted by spot-bonding on the membrane filter which was the second reagent layer (porous reagent layer) of the laminate, whereby an integral multi-layered analysis element (Element K) for the quantitative analysis of total cholesterol was prepared.

The spot-bonding was effected in a similar manner as described in Example 3.

As a Comparative Example, an integral multi-layered analysis element (Element L) was prepared similar to Element K except that a cellulose acetate membrane filter having a nominal pore size of 1.2 μm, a thickness of about 140 μm and a porosity of about 80% was used in place of the polyester circularly knitted velour cloth.

On each of the Elements K and L spotted was 20 μl of normal human whole blood (Hematocrit Value: 48%, Content of Total Cholesterol in the Blood Plasma: 151 mg/dl). Each element was incubated at 37° C. for 6 minutes, and immediately after incubation, the absorbency of the reflected light in the element was measured from the polyethylene terephthalate support side using visible lights having center wavelengths of 540 nm and 640 nm.

Ten samples were used for each element to repeat the measurement for ten times, and the average value and the standard deviation (SD) of the results of repeated measurement were calculated. The results are shown in Table 6.

TABLE 6

|  | 540 nm | | 640 nm | |
| --- | --- | --- | --- | --- |
|  | Element K | Element L | Element K | Element L |
| 1 | 0.087 | 0.477 | 1.008 | 0.371 |
| 2 | 0.086 | 0.512 | 1.003 | 0.302 |
| 3 | 0.080 | 0.500 | 1.000 | 0.357 |
| 4 | 0.077 | 0.507 | 0.997 | 0.328 |
| 5 | 0.084 | 0.492 | 1.010 | 0.397 |
| 6 | 0.084 | 0.476 | 1.005 | 0.348 |
| 7 | 0.088 | 0.504 | 1.000 | 0.386 |
| 8 | 0.079 | 0.490 | 1.003 | 0.320 |
| 9 | 0.085 | 0.482 | 0.994 | 0.366 |
| 10 | 0.082 | 0.510 | 1.007 | 0.339 |
| Average | 0.0825 | 0.4950 | 1.0027 | 0.3514 |
| SD | 0.0033 | 0.0129 | 0.0048 | 0.0284 |

The absorbency of the reflected light at 540 nm, i.e the absorbance by erythrocyte, was relatively high as 0.49 in the Element L to show insufficient separation of blood cells. In contrast thereto, the absorbency of the reflected light in the Element K, in which the napped cloth was used, was substantially same as the background level to show that erythrocyte was removed substantially completely without significant hemolysis.

The absorbency of the reflected light at 640 nm, i.e. the absorbance by the total cholesterol, was relatively high as 1.003 with insignificant scattering of the measured values (SD=0.005) in the Element K. On the contrary, in the Element L, the absorbancy of the reflected at 640 nm was relatively low as 0.351 with significant scattering of the values (SD=0.028). It is understood that hemolysis occurred and the dye forming reaction was inhibited in the Element L.

As seen from the results, the Element K prepared in accordance with the present invention exhibited improved blood cell separation function and improved resistance to hemolysis, and also exhibited excellent sensitivity and reproducibility at the measuring step.

Example 7 and Comparative Example 7
Preparation of an integral multi-layered analysis element for the quantitative analysis of glucose An analysis element M was prepared similar to Analysis Element A in Example 1, except that a micro-fibrous woven cloth was used in place of the non-woven cloth.

In detail, similar to Example 1, a PET sheet (serving as a support), a reagent layer, and a light-shielding layer were laminated in this order.

The surface of the light-shielding layer was uniformly wetted with water, and a micro-fibrous cloth (Average Filament Diameter: 5.3 μm, Porosity: 60%, Thickness: 200 μm), which was prepared by plain weaving polyester/nylon jaxtaposed multiple composite threads (100 warps/inch×100 wefts/inch) and then splitting the thus woven cloth by solvent extraction, was laminated on the wetted light-shielding layer while applying a uniform light pressure and then dried to form an integral multi-layered analysis element (Element M).

As a Comparative Example, an integral multi-layered analysis element (Element N) was prepared similar to Element M except that a cellulose acetate membrane filter having a nominal pore size (i.e. the effective pore size or the average value of smallest pore size) of 1.2 μm, a thickness of about 140 μm and a porosity of about 80% was used in place of the micro-fibrous cloth.

On each of the Elements M and N spotted was 20 μl of normal human whole blood (Hematocrit Value: 42%, Glucose content in the Blood Plasma: 122 mg/ml). Each element was incubated at 37° C. for 6 minutes, and immediately after incubation, the absorbency of the reflected light in the element was measured from the support side using visible lights having center wavelengths of 540 nm and 640 nm. Ten samples were used for each element to repeat the measurement for ten times, and the average value and the standard deviation (SD) of the results of repeated measurement were calculated. The results are shown in Table 7.

TABLE 7

|  | 540 nm | | 640 nm | |
| --- | --- | --- | --- | --- |
|  | Element M | Element N | Element M | Element N |
| 1 | 0.084 | 0.501 | 1.113 | 0.800 |
| 2 | 0.084 | 0.475 | 1.120 | 0.739 |
| 3 | 0.086 | 0.534 | 1.111 | 0.712 |
| 4 | 0.086 | 0.397 | 1.114 | 0.811 |
| 5 | 0.084 | 0.487 | 1.113 | 0.744 |
| 6 | 0.085 | 0.362 | 1.121 | 0.762 |
| 7 | 0.083 | 0.452 | 1.114 | 0.798 |
| 8 | 0.087 | 0.400 | 1.112 | 0.722 |
| 9 | 0.082 | 0.439 | 1.116 | 0.762 |
| 10 | 0.086 | 0.491 | 1.118 | 0.805 |
| Average | 0.0847 | 0.4538 | 1.1152 | 0.7655 |
| SD | 0.0015 | 0.0513 | 0.0032 | 0.0344 |

The absorbency of the reflected light at 540 nm, i.e. the absorbance by hemoglobin contained in the erythrocyte, was substantially negligible in the Element M in which the micro-fibrous cloth was used. On the contrary, the absorbancy of the reflected light at 540 nm in the Element N of Comparative Example 7 was relatively high as about 0.454, which revealed that separation of blood cells was insufficient or hemolysis occurred in the Element N. In contrast thereto, red blood cells were removed substantially completely and hemolysis did not take place in the Element M in which the micro-fibrous cloth was used.

On the other hand, the absorbency of the reflected light at 640 nm, i.e. the absorbance by glucose in the blood plasma, was relatively high as 1.115 in the Element M, with insignificant scattering of the measured data (SD=0.003). On the contrary, the absorbency of the reflected light at 640 nm was lowered to 0.766 in the Element N, with significant scattering of the measured data (SD=0.034). The result showed that hemolysis occurred in the Element N to inhibit dye forming reaction.

The element M prepared by the present invention exhibited improved blood cell separation function and improved resistance to hemolysis. It was also excellent in sensitivity and reproducibility at the measuring step.

Example 8 and Comparative Example 8
Preparation of an integral multi-layered analysis element for the quantitative analysis of total bilirubin An analysis element O was prepared similar to Analysis Element C in Example 2, except that a micro-fibrous woven cloth was used in place of the non-woven cloth.

In detail, similar to Example 2, a PET sheet (serving as a support), a first water-absorbing layer, a second water-absorbing layer, and a porous reagent (woven cloth) layer were laminated successively, and a light-shielding layer was formed at the surface portion of the porous reagent layer.

A microfilament cloth (Average Filament Diameter: 4.5 μm, Porosity: 68%, Thickness: 130 μm), which was prepared by plain weaving polyester/polyethylene sea-island structured multiple composite threads (100 warps/inch×100 wefts/inch) and then splitting the thus woven cloth by solvent extraction to leave polyester microfilaments, was laminated on the woven cloth (porous reagent layer) to form an integral multi-layered analysis element (Element O).

As a Comparative Example, an integral multi-layered analysis element (Element P) was prepared similar to Element O except that a cellulose acetate membrane filter having a nominal pore size of 1.2 μm, a thickness of about 140 μm and a porosity of about 80% was used in place of the polyester micro-fibrous cloth.

On each of the elements O and P spotted was 20 μl of normal human whole blood (Hematocrit Value: 42%, Content of Total Bilirubin in the Blood Plasma: 0.98 mg/dl). Each element was incubated at 37° C. for 6 minutes, and immediately after incubation, the absorbancy of the reflected light in the element was measured from the support side using visible lights having center wavelengths of 600 nm and 540 nm.

Ten samples were used for each element to repeat the measurement for ten times, and the average value and the standard deviation (SD) of the results of repeated measurement were calculated. The results are shown in Table 8.

TABLE 8

|  | 600 nm | | 540 nm | |
| --- | --- | --- | --- | --- |
|  | Element O | Element P | Element O | Element P |
| 1 | 0.608 | 0.344 | 0.862 | 1.003 |
| 2 | 0.612 | 0.331 | 0.864 | 0.989 |
| 3 | 0.607 | 0.399 | 0.870 | 1.078 |
| 4 | 0.611 | 0.367 | 0.866 | 1.045 |
| 5 | 0.615 | 0.320 | 0.866 | 0.991 |
| 6 | 0.609 | 0.382 | 0.867 | 1.012 |
| 7 | 0.610 | 0.360 | 0.861 | 1.114 |
| 8 | 0.612 | 0.303 | 0.864 | 1.170 |
| 9 | 0.611 | 0.356 | 0.865 | 0.972 |
| 10 | 0.613 | 0.342 | 0.868 | 0.965 |
| Average | 0.6108 | 0.3504 | 0.8653 | 1.0339 |
| SD | 0.0023 | 0.0272 | 0.0026 | 0.0639 |

The absorbency of the reflected light at 600 nm, i.e the absorbance by the formed dye, was relatively high as 0.611 with insignificant scattering of the data (SD=0.002) in the Element O. In the Element P, the absorbancy of the reflected light at 600 nm was relatively low as 0.350 with significant scattering (SD=0.027). The result revealed that hemolysis occurred in the Element P to inhibit the dye forming reaction.

The absorbency of the reflected light at 540 nm is the sum of the absorbance by the formed dye and the absorbance by the red blood cell. The absorbance at 540 nm was 0.865 in the Element O, and that in the Element P was 1.034 which was higher than the absorbance in the Element O. As seen, in the Element P, the absorbance at 600 nm was low to show that the quantity of the formed dye was small, whereas the absorbance at 540 nm was high. This revealed that the blood cells were separated only insufficiently in the Element P. In contrast thereto, the Element O prepared in accordance with this invention exhibited improved blood cell separation function and improved resistance to hemolysis, and also exhibited excellent sensitivity and reproducibility at the measuring step.

Example 9 and Comparative Example 9
Preparation of an integral multi-layered analysis element for the quantitative analysis of total cholesterol An analysis element Q was prepared similar to Analysis Element E in Example 3, except that a micro-fibrous woven cloth was used in place of the non-woven cloth.

In detail, similar to Example 3, a PET sheet (serving as a support), a first reagent layer (coloring reagent layer) and a second reagent layer (porous reagent layer) were laminated successively.

Then, by gravure printing process, a micro-fibrous woven cloth prepared by plain weaving nylon threads each having an average filament diameter of 4.5 μm (100 warps/inch× 100 wefts/inch) and having a porosity of 50% and a thickness of 150 μm was fitted on the porous reagent layer (membrane filter), whereby an integral multi-layered analysis element (Element Q) for the quantitative analysis of total cholesterol was prepared.

The spot-bonding was effected in a similar manner as described in Example 3.

As a Comparative Example, an integral multi-layered analysis element (Element R) was prepared similar to Element Q except that a cellulose acetate membrane filter having a nominal pore size of 1.2 μm, a thickness of about 140 μm and a porosity of about 80% was used in place of the nylon micro-fibrous cloth.

On each of the Elements Q and R spotted was 20 μl of normal human whole blood (Hematocrit Value: 48%, Content of Total Cholesterol in the Blood Plasma: 1.51 mg/dl). Each element was incubated at 37° C. for 6 minutes, and immediately after incubation, the absorbency of the reflected light in the element was measured from the polyethylene terephthalate support side using visible lights having center wavelengths of 540 nm and 640 nm.

Ten samples were used for each element to repeat the measurement for ten times, and the average value and the standard deviation (SD) of the results of repeated measurement were calculated. The results are shown in Table 9.

TABLE 9

|  | 540 nm | | 640 nm | |
| --- | --- | --- | --- | --- |
|  | Element Q | Element R | Element Q | Element R |
| 1 | 0.074 | 0.482 | 1.011 | 0.350 |
| 2 | 0.071 | 0.490 | 1.015 | 0.337 |
| 3 | 0.069 | 0.508 | 1.010 | 0.371 |
| 4 | 0.076 | 0.511 | 1.013 | 0.358 |
| 5 | 0.075 | 0.487 | 1.012 | 0.321 |
| 6 | 0.069 | 0.477 | 1.010 | 0.380 |
| 7 | 0.072 | 0.496 | 1.013 | 0.328 |
| 8 | 0.075 | 0.489 | 1.017 | 0.395 |
| 9 | 0.068 | 0.501 | 1.008 | 0.362 |
| 10 | 0.072 | 0.468 | 1.014 | 0.342 |
| Average | 0.0721 | 0.4909 | 1.0123 | 0.3544 |
| SD | 0.0027 | 0.0128 | 0.0025 | 0.0222 |

The absorbency of the reflected light at 540 nm, i.e the absorbance by erythrocyte, was relatively high as 0.491 in the Element R to show insufficient separation of blood cells. In contrast thereto, the absorbancy of the reflected light in the Element Q, in which the micro-fibrous cloth was used, was substantially same as the background level to show that red blood cell was removed substantially completely without significant hemolysis.

The absorbency of the reflected light at 640 nm, i.e. the absorbance by the total cholesterol, was relatively high as 1.012 with insignificant scattering of the measured values (SD=0.003) in the Element Q. On the contrary, in the Element R, the absorbency of the reflected at 640 nm was relatively low as 0.354 with significant scattering of the values (SD=0.022). It is understood that hemolysis occurred and the dye forming reaction was inhibited in the Element R.

As seen from the results, the Element Q prepared in accordance with the present invention exhibited improved blood cell separation function and improved resistance to hemolysis and also exhibited excellent sensitivity and reproducibility at the measuring step.

As should be appreciated from the foregoing, the integral multi-layered analysis element provided by this invention exhibits an improved in blood cell separation function and also improved in resistance to hemolysis, by the action of the volume filtrating layer comprised of a material selected from the micro-fibrous cloths and napped cloth as described in detail hereinbefore and defined in the claims. The data obtained by the use of the integral multi-layered analysis element of the invention are not scattered and improved in reproducibility. Since the micro-fibrous non-woven cloths or napped cloths used to form the volume filtrating layer are not fragile, they are easily produced and handled. The integral multi-layered analysis element of the invention allows the use of whole blood directly without any preparatory processing as a sample liquid.

What is claimed is:

1. A dry analysis element for the quantitative analysis of an analyte contained in whole blood, consisting essentially of:
   a blood filtration layer consisting of a layer of cloth selected from a micro-fibrous cloth made of non-glass fibers having an average fiber diameter of from 0.1 to 10 μm, or a napped cloth, each of the napped fibers of said napped cloth being non-glass fibers and having an average diameter of from 1 to 30 μm, and
   a detection layer laminated with said blood filtration layer;
   whereby plasma is separated from the whole blood through said blood filtration layer while avoiding hemolysis of red blood cells and is received by said detection layer, wherein the analyte in the plasma is detected in said detection layer.

2. The dry analysis element according to claim 1, wherein said micro-fibrous cloth is a non-woven cloth having a density of from 0.01 to 0.2 g/cm$^3$ and made of fibers each having an average fiber diameter of from 0.2 to 10 μm and the detection layer laminated with said non-woven cloth.

3. The dry analysis element according to claim 2 wherein said non-woven cloth and said detection layer are substantially intimately to form an integral structure by an adhesive arranged partially or discontinuously on an interface between both layers so as not to significantly inhibit the uniform permeation of liquid and the analyte therethrough.

4. The dry analysis element according to claim 2, wherein said detection layer comprises at least one reagent layer and a separate detection layer.

5. The dry analysis element according to claim 2, further comprising a porous layer interposed between said non-woven cloth and said detection layer.

6. The dry analysis element according to claim 5, wherein said non-woven cloth and said interposed porous layer are bonded substantially intimately to form an integral structure by an adhesive arranged partially or discontinuously on an interface between both layers so as not to significantly inhibit the uniform permeation of liquid and the analyte therethrough.

7. The dry analysis element according to claim 5, wherein said detection layer comprises at least one reagent layer and a separate detection layer.

8. The dry analysis element according to claim 1, wherein said napped cloth has a fiber density per cm$^2$ of from $7.0 \times 10^3$ to $8.2 \times 10^6$, and the detection layer is laminated with said napped cloth, each of the napped fibers of said napped cloth having an average diameter of from 1 to 30 μm and an average nap length of 0.5 to 5.0 mm.

9. The dry analysis element according to claim 8, wherein said napped cloth and said detection layer are bonded substantially intimately to form an integral structure by an adhesive arranged partially or discontinuously on an interface between both layers so as not to significantly inhibit the uniform permeation of liquid and the analyte therethrough.

10. The dry analysis element according to claim 8, wherein said detection layer comprises at least one reagent layer and the detection layer.

11. The dry analysis element according to claim 8, wherein the average nap length L in μm units of the napped fibers of said napped cloth is selected such that the interrelationship between the average nap length L and the volume V in μl units of spotted whole blood is maintained within the following range of:

$$5 \leq L/V \leq 200.$$

12. The dry analysis element according to claim 8, further comprising a porous layer interposed between said napped cloth and said detection layer.

13. The dry analysis element according to claim 12, wherein said napped cloth and said interposed porous layer are bonded substantially intimately to form an integral structure by an adhesive arranged partially or discontinuously on an interface between both layers so as not to significantly inhibit the uniform permeation of liquid and the analyte therethrough.

14. The dry analysis element according to claim 12, wherein said detection layer comprises at least one reagent layer and a separate detection layer.

15. The dry analysis element according to claim 12, wherein the average nap length L in μm units of the napped fibers of said napped cloth is selected such that the interrelationship between the average nap length L and the volume V in μl unity of spotted whole blood is maintained within the following range of:

$$5 \leq L/V \leq 200.$$

16. The dry analysis element according to claim 1, wherein said micro-fibrous cloth having a porosity of from 45 to 70% and made of micro filaments each having an average filament diameter of from 0.1 to 7 μm, and a detection layer laminated with said cloth.

17. The dry analysis element according to claim 16, wherein said cloth and said detection layer bonded substantially intimately to form an integral structure by an adhesive arranged partially or discontinuously on an interface between both layers so as not to significantly inhibit the uniform permeation of liquid and the analyte therethrough.

18. The dry analysis element according to claim 16, wherein said detection layer comprises at least one reagent layer and a separate detection layer.

19. The dry analysis element according to claim 16, further comprising a porous layer interposed between said cloth and said detection layer.

20. The dry analysis element according to claim 19, wherein said cloth and said interposed porous layer are bonded substantially intimately to form an integral structure by an adhesive arranged partially or discontinuously on an interface between both layers so as not to significantly inhibit the uniform permeation of liquid and the analyte therethrough.

21. The dry analysis element according to claim 19, wherein said detection layer comprises at least one reagent layer and a separate detection layer.

* * * * *